United States Patent [19]

DeLuca et al.

[11] 4,292,250
[45] Sep. 29, 1981

[54] VITAMIN D DERIVATIVES

[75] Inventors: Hector F. DeLuca; Heinrich K. Schnoes; Leon W. LeVan, all of Madison, Wis.

[73] Assignee: Wisconsin Alumni Research Foundation, Madison, Wis.

[21] Appl. No.: 207,169

[22] Filed: Nov. 17, 1980

[51] Int. Cl.³ .............................................. C07J 9/00
[52] U.S. Cl. ................................................ 260/397.2
[58] Field of Search ...................................... 260/397.2

[56] References Cited

U.S. PATENT DOCUMENTS 4,119,647 10/1978 Liebman et al. ................. 260/397.2
4,230,627 10/1980 DeLuca et al. .................. 260/397.2

Primary Examiner—Elbert L. Roberts
Attorney, Agent, or Firm—Howard W. Bremer

[57] ABSTRACT

The invention provides new 25-hydroxy vitamin $D_2$ 25-glucuronide derivatives among which is 25-hydroxy vitamin $D_2$ 25-D-glucuronic acid.

By virtue of the structural similarity of 25-hydroxy vitamin $D_2$ 25-D-glucuronic acid to 25-hydroxy vitamin $D_2$, a known biologically potent compound, the glucuronic acid compound should be a ready substitute for 25-hydroxy vitamin $D_2$ in various therapeutic applications and particularly where the water solubility of the glucuronic acid compound is a necessity or advantage.

3 Claims, No Drawings

VITAMIN D DERIVATIVES

DESCRIPTION

The invention described herein was made in the course of work under a grant or award from the Department of Health, Education and Welfare.

TECHNICAL FIELD

This invention relates to a novel derivative of vitamin D.

More specifically this invention relates to a novel derivative of vitamin $D_2$.

It is now widely accepted that both vitamin $D_3$ and vitamin $D_2$ must be 25-hydroxylated in the liver as the first step in their conversion to the 1,25-dihydroxylated compounds, which are generally considered to be the physiologically active or hormonal forms of the vitamins, and to be responsible for what are termed the vitamin D-like activities, such as increasing intestinal absorption of calcium and phosphorous, mobilizing bone mineral and retaining calcium in the kidneys.

BACKGROUND ART

References to various vitamin D derivatives are extant in the patent and other literature. See, for example, U.S. Pat. Nos.: 3,565,924 directed to 25-hydroxycholecalciferol; 3,697,559 directed to 1,25-dihydroxycholecalciferol; U.S. Pat. No. 3,741,996 directed to 1α-hydroxycholecalciferol; U.S. Pat. No. 3,907,843 directed to 1α-hydroxygocalciferol; U.S. Pat. No. 3,715,374 directed to 24,25-dihydroxycholecalciferol; U.S. Pat. No. 3,739,001 directed to 25,26-dihydroxycholecalciferol; U.S. Pat. No. 3,786,062 directed to 22-dehydro-25-hydroxycholecalciferol; U.S. Pat. No. 3,847,955 directed to 1,24,25-trihydroxycholecalciferol; U.S. Pat. No. 3,906,014 directed to 3-deoxy-1α-hydroxycholecalciferol; U.S. Pat. No. 4,069,321 directed to the preparation of various side chain fluorinated vitamin $D_3$ derivatives and side chain fluorinated dihydrotrachysterol$_3$ analogs.

Although earlier studies have reported vitamin $D_3$-like metabolites in bile more polar than 25-hydroxy vitamin $D_3$ or 1,25(OH)$_2D_3$, none of such metabolites has been positively identified (see Avioli et al, J. Clin. Invest. 46, 983–992 (1967); Bell et al, Biochem. J. 115, 663–669 (1969); Imrie et al, Arch. Biochem. Biophys. 120, 525–532 (1967). Bell et al report that the major metabolite of vitamin D found in rat bile appears to be a glucuronide conjugate not identical with synthetic cholecalciferyl glucuronide.

Disclosure of Invention

New derivatives of vitamin $D_2$ have now been found amoung which is 25-hydroxy vitamin $D_2$ 25-D-glucuronic acid. Inasmuch as this compound is an analog of the biologically potent 25-hydroxy vitamin $D_2$ (see U.S. Pat. No. 3,907,843), by virtue of such structural similarity, it should find application as a substitute for 25-hydroxy vitamin $D_2$ in various therapeutic applications, particularly those involving calcium-phosphorous imbalance. In this regard the compound of this invention offers additional advantages in that it is water soluble. Hence, it lends itself to intravenous and intramuscular dosage formulations and to administration to patients who have difficulty in assimilating lipids.

The glucuronic acid compound of this invention can be represented by the following structure:

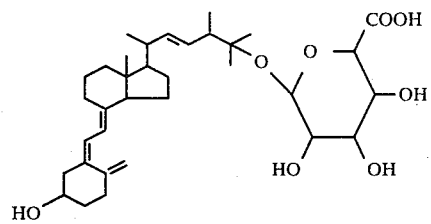

BEST MODE FOR CARRYING OUT THE INVENTION

Experimental Procedure

In the following description the abbreviations used are:

HPLC, high pressure liquid chromatography; $CH_2N_2$, diazomethane; DEAE, diethylaminoethyl; BSTFA, a formulation of 1% trimethyl chlorosilane in bis(trimethylsilyl)-trifluoroacetamide; TMS, trimethylsilyl $(CH_3)_3Si$; 25-OH-D, 25-hydroxyvitamin D; 1,25-(OH)$_2$D, 1,25-dihydroxyvitamin D; 25-OH-D$_2$, 25-hydroxy-vitamin D$_2$; UV, ultraviolet.

General Procedures

Radioactivity was determined by liquid scintillation counting with a Packard Model 3255 liquid scintillation counter equipped with automatic external standardization for determining counting efficiency. Aqueous samples were counted in Aquasol (New England Nuclear, Boston, MA) while other samples were counted in a toluene solution containing 0.2% 2,5-diphenyloxazole and 0.01% 1,4-bis[2-(4-methyl-5-phenyloxazolyl)]benzene.

High-pressure liquid chromatography (HPLC) was carried out with a Waters Model ALC/GPC 204 liquid chromatograph equipped with a Waters Model 440 absorbance detector operating at 254 nm. For reversed-phase HPLC either a 0.94×25 cm Partisil-10 ODS-2 semipreparative column (Whatman Inc., Clifton, NJ) or a 0.46×25 cm Zorbax-ODS analytical column (DuPont Company, Wilmington, DE) was used. For straight-phase HPLC a 0.46×25 cm Zorbax-SIL analytical column (DuPont Co.) was employed. HPLC-grade solvents were obtained from Fisher Chemical Co. (Chicago, IL); the solvent systems used are noted below.

Ultraviolet (UV) absorption spectra were recorded with a Beckman Model 24 recording spectophotometer. Mass spectrometry was performed with an A.E.I. MS-9 mass spectrometer equipped with a DS-50 data acquisition system, using electron impact ionization (70 eV) and direct probe sample introduction at 130°–160° C. above ambient.

Chemicals

Vitamin $D_2$ was obtained from the Thompson-Hayward Chemical Co. (Kansas City, KS); its purity was ascertained by UV absorption spectroscopy. 3α-[$^3$H]-vitamin $D_2$ of specific activity 1.9 Ci/mmol was synthesized. This compound exhibited the characteristic vitamin D cis-triene UV absorption spectrum and comigrated with authentic vitamin $D_2$ on both straight-phase HPLC (Zorbax-SIL column eluted with 1% isopropanol in hexane) and reversed-phase HPLC (Zorbax-ODS column eluted with 2% water in methanol). The tritiated vitamin $D_2$ was purified at the onset of this study by chromatography on silica gel eluted with hexane-ether 60:40 followed by chromatography on Lipidex 5000 (Packard Instrument Co., Downers Grove, IL) eluted with hexane-chloroform 95:5. Aliquots of the purified $^3H$-vitamin $D_2$ subjected to HPLC with the above systems indicated greater than 98% radiochemical purity.

All chemicals and solvents used were reagent grade. Diazomethane ($CH_2N_2$) in ether solution was prepared by hydrolysis of N-methyl-N-nitroso-p-toluenesulfonamide in a Diazald kit (Aldrich Chemical Co., Milwaukee, WI). The silylating reagent BSTFA, a formulation of bis(trimethylsilyl)trifluoroacetamide containing 1% trimethylchlorosilane, was obtained from Pierce Chemical Co. (Rockford, IL). Beta-glucuronidase (bovine liver type B1) was purchased from Sigma Chemical Co. (St. Louis, MO). Sephadex LH-20 and DEAE-Sephadex A-25 are products of Pharmacia Fine Chemicals (Piscataway, NJ). The DEAE-Sephadex was used in the acetate form, prepared by slurrying the gel in a large excess of 1 M ammonium acetate in methanol followed by thorough washing with methanol.

Animals

One-day old white Leghorn cockerels were obtained from Northern Hatcheries (Beaver Dam, WI). They were maintained on a vitamin D-deficient soy protein diet containing 1.2% calcium and 0.47% phosphorus for eight weeks prior to use (Omdahl et al, Biochemistry 10, 2935-2940, 1971).

Generation of Vitamin $D_2$ Bile Metabolites $^3H$-vitamin $D_2$ doses were prepared by diluting purified $^3H$-vitamin $D_2$ with nonradioactive vitamin $D_2$ to give a specific activity of 20 mCi/mmol (114,000 dpm/$\mu$g) and dissolving in 95% ethanol. A group of 20 chickens each received by wing-vein injection, 250 $\mu$g of $^3H$:vitamin $D_2$ in 50 $\mu L$ of 95% ethanol. Food was withheld from the chickens for 6 hours prior to dosing and they were fasted for the duration of the experiment. At 24 hours after dosing the chickens were killed, their gall bladders removed and cut open to yield bile. The bile (39 mL) was diluted with distilled water and aliquots were taken for radioactivity determination. The diluted bile was then lyophilized to dryness and the resulting solids were extracted with 200 mL of methanol. The methanol extract was filtered to remove insoluble material; the filter paper and residue were thoroughly washed with several portions of methanol which were then combined with the original filtrate. This combined methanol extract was concentrated in a rotary evaporator and used for chromatography.

Chromatography of Methanol Extract

The methanol extract was applied to a 3×22 cm column of DEAE-Sephadex A-25 (acetate form) in methanol. Neutral compounds were eluted with methanol (200 ml.), and the eluting solvent was then changed to 0.4 M ammonium acetate in methanol (400 mL) in order to elute charged compounds. Five-mL fractions were collected and a 25 $\mu L$ aliquot of each used for scintillation counting. The column profile in elution order evinced two peaks. Peak I contained the neutral metabolites and Peak II contained the charged metabolities. Fractions under these two peaks were respectively pooled.

The Peak II metabolites were concentrated and applied to a 2×78 cm column of Sephadex LH-20 eluted with methanol. A single peak of radioactivity was observed, and the radioactive fractions (5.0 mL fractions) were pooled for further chromatography. (In the foregoing and following description involving pooling of chromatographic fractions the precise fractions pooled are not indicated since there can vary depending upon column preparation, elution volumes and other variables).

HPLC of Peak II (Charged) Metabolites

Following Sephadex LH-20 chromatography the Peak II charged metabolites were concentrated and divided into 4 equal portions. Each portion was subjected to HPLC on a Partisil ODS-2 semi-preparative column eluted with methanol:water 65:35 containing 10 mM ammonium bicarbonate. The flow rate was 4 ML/min and 4.0 mL fractions were collected; a 100 $\mu L$ aliquot of each was used for scintillation counting. Several radioactive peaks (designated by the letters A–D in elution order ) were present in the column profiles. For each run, the fractions corresponding to Peak C were pooled and the Peak C regions from all four HPLC runs were then combined.

The Peak C fraction was next subjected to HPLC on a Zorbax-ODS analytical column eluted with the same solvent at a flow rate of 2 mL/min and operated in the recycle mode. A total of six passes through the column was required to resolve the radioactive Peak C from two other UV-absorbing peaks. On the final pass the Peak C fraction was collected, concentrated, and used for characterization. The UV absorption spectrum of this compound in methanol showed the characteristic vitamin D absorption band at $\lambda_{max}=265$ nm. Based on the UV spectrum and radioactivity measurements, a total of 19 nmole of the Peak C metabolite was obtained.

Hydrolysis of Metabolite C

The metabolite was hydrolyzed by mild acid-catalyzed hydrolysis in tetrahydrofuran, a method developed for acid-sensitive steroid glucuronides (Burstein et al, Chem. Soc. 82, 1226–1230 (1960); Jacobson & Lieberman, J. Biol. Chem. 237, 1469–1475 (1962). 5 nmol of the Peak C metabolite as treated with 200 $\mu L$ of 0.01 N perchloric acid in tetrahydrofuran for 80 hours at room temperature ($\sim 22°$ C.). After neutralization with 1% aqueous sodium bicarbonate, the reaction mixture was evaporated to dryness under nitrogen and the residue was applied to an HPLC system consisting of a Zorbax-ODS column eluted with methanol:water 90:10. With this system unreacted metabolite eluted at 4 mL and the reaction product which eluted at 17 mL. was collected. Following evaporation to dryness, the hydrolyis product was dissolved in methanol and its UV absorption spectrum was recorded. The product was then subjected to final purification on a Zorbax-SIL column eluted with 4% isopropanol in hexane, and the material from this run (elution volume=18 mL) was collected and used for mass spectrometry.

Treatment of Metabolite C with $\beta$-Glucuronidase

The metabolite (0.25 nmole) was incubated with 500 Fishman units of $\beta$-glucuronidase (bovine liver type B1) in 1.0 ml of 0.1 M sodium acetate buffer, pH 5.0, for 3 hours at 37° C. Ether (1.5 mL) was then added and the mixture was vortexed thoroughly then allowed to separate. Aliquots of each phase were used for radioactivity determination. A control incubation was performed in an identical fashion except the enzyme was heated in a boiling water bath for 5 minutes prior to incubation. The distribution of radioactivity between the organic and aqueous phases is shown in Table I.

TABLE I

| Action of $\beta$-Glucuronidase on Metabolite "C" | | |
|---|---|---|
| Incubation | DPM in Aqueous Phase | DPM in Ether Phase |
| Active Enzyme | 2955 (42%) | 4069 (58%) |
| Boiled Enzyme | 3784 (72%) | 1476 (28%) |

Chemical Modifications of Metabolite C a. Esterification with diazomethane. The metabolite, dissolved in 50 µL of methanol, was treated with excess diazomethane in ether for 10 minutes at room temperature. Excess diazomethane and solvents were removed by evaporating the reaction mixture on a Zorbax-ODS column eluted with methanol:water 85:15 easily separated the less polar methylated metabolite (elution volume approximately 19 mL) from unreacted starting material (elution volume approximately 4 mL) and other impurities. In a subsequent experiment the yield of methylated product was enhanced by including 5 µL of formic acid in the reaction mixture prior to adding diazomethane, although more of the latter must then be used. In either case the methylated metabolite exhibited an unaltered vitamin D UV absorption spectrum with $\lambda_{max} = 265$ nm. Attempts to purify this compound further by straight-phase HPLC on silica columns proved unsuccessful.

b. Trimethylsilyl ether formation. The methylated metabolite (5 nmol) from (a) was treated with 50 µL of BSTFA and 50 µL of dry pyridine for 1 hour at 50° C. under nitrogen. After evaporation to dryness under a stream of nitrogen, the reaction mixture was dissolved in hexane and applied to HPLC. With a system consisting of a Zorbax-SIL column eluted with 0.1% isopropanol in hexane, the silylated metabolite eluted as a single peak at about 18 mL and was collected for mass spectrometry.

c. Acetylation of metabolite. The methylated metabolite (3 nmol) from (2) was treated with 50 µL of acetic anhydride and 50 µL of dry pyridine for 4 hours at room temperature. After evaporation of the solvent to dryness under nitrogen, the product was subjected to HPLC on a Zorbax-SIL column eluted with 4% isopropanol in hexane. A single peak eluting at 17 mL was observed with the UV monitor; this material was collected and used for mass spectrometry.

Results

The bile obtained 24 hours after dosing contained 6.5% of the total administered radioactivity. Chromatography of the methanol extract of bile on DEAE-Sephadex separated the radioactivity into a minor neutral fraction and a major charged fraction containing 28% and 72% respectively of the radioactivity recovered from the column. The charged fraction yielded a single peak upon Sephadex LH-20 gel filtration chromatography; recovery of radioactivity from this column was greater than 90%. Reversed-phase HPLC of the peak recovered from Sephadex LH-20 resolved this charged material into several peaks (designated A-D in elution order), with the peak designated C accounting for approximately 9% of the charged metabolites. Further HPLC with other reversed-phase systems demonstrated that only Peaks C and D were radioactively homogeneous, while the more polar peaks A and B contained a number of radioactive metabolites. At physiologic dose levels (250 ng) of $^3$H-vitamin $D_2$, peak C was found to be the most abundant charged metabolite and was therefore chosen for characterization.

Identification of Metabolite C

The purified peak C metabolite exhibited the UV absorbance spectrum ($\lambda_{max} = 265$ nm) characteristic of the vitamin D cis-triene system, therefore, this feature must be present in the isolated metabolite. Retention of the compound by DEAE-Sephadex indicated the presence of an acidic function. The acidic nature of the metabolite was confirmed by its reaction with diazomethane, characteristic of carboxyl groups. After methylation the metabolite behaved as a neutral compound on DEAE-Sephadex and retained the characteristic vitamin D UV spectrum, indicating that diazomethane reacted with the carboxyl function and not with the triene system in any way.

The metabolite was identified as a hexuromic acid conjugate of 25-hydroxy-vitamin $D_2$ by the following evidence: When the metabolite was subjected to acid-catalyzed hydrolysis under mild conditions the vitamin D-moiety was liberated for independent characterization. The chromatographic properties and UV and mass spectra of the vitamin D-aglycone thus obtained clearly identified this compound as 25-hydroxy vitamin $D_2$ (25-OH-$D_2$). With both HPLC systems used for purification, the compound eluted at exactly the same position as synthetic 25-OH-$D_2$. The UV spectrum exhibited the characteristic vitamin D absorption with $\lambda_{max} = 265$ nm, $\lambda_{min} = 228$ nm, with the mass spectrum showing excellent agreement with the mass spectrum of 25-OH-$D_2$ (Suda et al, Biochemistry 8, 3515-3519 (1969). Incubation of the original metabolite with $\beta$-glucuronidase resulted in a significant increase in ether-soluble radioactivity (Table 1), suggesting that the metabolite was a glucuronide conjugate of 25-hydroxy vitamin $D_2$.

Mass spectrometry of the intact metabolite could be performed only after esterification of the carboxyl function and silylation or acetylation of hydroxyl groups. The mass spectrum of the silylated metabolite methyl ester exhibited a molecular ion at m/e 890, consistent with the calculated molecular weight of 890 for the tetra(trimethylsilyl) derivative of 25-OH-$D_2$ hexuronide methyl ester. The ion at m/e 407 represents the tris(-trimethylsilyl)-glucuronic acid methyl ester fragment resulting from cleavage of the glycosidic bond at C(1) of the glucuronic acid; loss of 90 (TMS-OH) from this fragment produces the very intense peak at m/e 317. The latter ion is characteristic of silylated glucuronides and is usually the base peak in the mass spectra of such compounds (Billets et al, J. Med. Chem. 16, 30–33 (1973). The ions at m/e 204 (HC-OTMS)$_2$ and m/e 217 [(HC-OTMS)$_2$CH] are common to all silylated carbohydrates, while the ion at m/e 275 is the carboxymethyl analog of the ion at m/e 217 (Billets et al, 1973). Elimination of the entire glucuronic acid moiety with charge retention on the vitamin $D_2$ fragment gives rise to the ion at m/e 466. Of interest is the ion at m/e 343, the silylated analog of the vitamin $D_2$ fragment at m/e 271 which arises by loss of the side chain by cleavage of the C(17)-C(20) bond. The presence of the m/e 343 ion indicates silylation of the 3-hydroxyl group and implies the presence of a free C-3-hydroxy group in the original metabolite. Consequently, the glucuronic acid must be conjugated to the 25-hydroxy group of the vitamin aglycon. That the side chain hydroxy function is blocked to silylation is also indicated by the absence of a peak at m/e 131 [$(CH_3)_2C=OTMS^+$], which is always the base peak in the mass spectra of the trimethylsilyl derivatives of 25-hydroxy-calciferols.

Additional evidence that the glucuronic acid is located at the 25-position is provided by the mass spectrum of the acetylated metabolite methyl ester. This compound exhibits a weak molecular ion at m/e 770 whose identity is confirmed by more prominent peaks at m/e 710 and m/e 650 resulting from the loss of one and two molecules, respectively, of acetic acid (MW=60) from the molecular ion. A molecular weight of 770 indicates addition of four acetyl groups to 25-OH-$D_2$25-glucuronide methyl ester, reflecting acetylation at C-2', C-4', and C-4' of glucuronic acid and at C-3 of the 25-OH-$D_2$ moiety. Acetylation of the alternative conjugate, 25-OH-$D_2$-3-glucuronide, would yield a triacetyl derivative with a molecular weight of 728 since the tertiary 25- hydroxyl is not acetylated under the mild reaction conditions employed here. Under the same conditions authentic 25-OH-$D_2$ gave only the 3-monoacetylated product as determined by HPLC and mass spectrometry; indeed, acetylation of the 25-hydroxyl requires much more vigorous conditions. Thus, the formation of the acetylated derivative with molecular weight of 770 supports the conclusion of a blocked 25-hydroxyl function and an available 3-hydroxyl group and, therefore, requires a 25-glucuronide structure for the metabolite. In addition, cleavage of the metabolite by $\beta$-glucuronidase implies a $\beta$-glycosidic linkage at C-1 of the glucuronic acid, since $\beta$-glucuronidase is specific for the $\beta$-glycoside configuration of glucuronic acid. Thus the metabolite is 25-OH-$D_2$ 25-$\beta$-glucuronide.

It can be concluded from the foregoing that, unexpectedly, 25-hydroxy vitamin $D_2$ is the compound in the bile rather than vitamim $D_2$ itself and that, also unexpectedly, glucuronylation occurs at the fairly hindered 25-position.

We claim:
1. Compounds having the formula

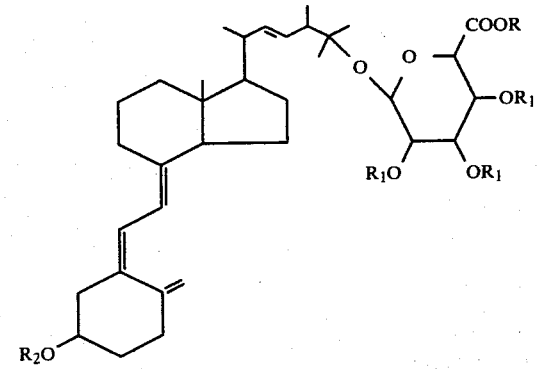

where
R is a hydrogen or methyl, $R_1$ is trimethylsilyl or acetyl and
$R_2$ is hydrogen, trimethylsilyl or acetyl.
2. 25-hydroxy vitamin $D_2$ 25-D-hexuronic acid.
3. 25-hydroxy vitamin $D_2$ 25-$\beta$-D-glucuronide.

* * * * *